(12) United States Patent
Koh et al.

(10) Patent No.: US 7,548,785 B2
(45) Date of Patent: Jun. 16, 2009

(54) COLLECTING AND ANALYZING SENSED INFORMATION AS A TREND OF HEART FAILURE PROGRESSION OR REGRESSION

(75) Inventors: Steve Koh, South Pasadena, CA (US); Euljoon Park, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 647 days.

(21) Appl. No.: 10/866,422

(22) Filed: Jun. 10, 2004

(65) Prior Publication Data
US 2005/0277992 A1 Dec. 15, 2005

(51) Int. Cl.
*A61N 1/362* (2006.01)
(52) U.S. Cl. .......................... 607/18; 607/19; 600/509
(58) Field of Classification Search ............. 607/18–19; 600/509
See application file for complete search history.

(56) References Cited

U.S. PATENT DOCUMENTS

| | | | | |
|---|---|---|---|---|
| 4,712,555 A | 12/1987 | Thornander et al. | ... | 128/419 PG |
| 4,788,980 A | 12/1988 | Mann et al. | ......... | 128/419 PG |
| 4,940,052 A | 7/1990 | Mann et al. | ......... | 128/419 PG |
| 4,944,298 A | 7/1990 | Sholder | ................ | 128/419 PG |
| 5,215,098 A * | 6/1993 | Steinhaus et al. | ........... | 600/515 |
| 5,462,060 A | 10/1995 | Jacobson et al. | ............ | 128/702 |
| 5,466,254 A | 11/1995 | Helland | ....................... | 607/123 |
| 5,476,483 A | 12/1995 | Bornzin et al. | ................ | 607/17 |
| 5,999,854 A * | 12/1999 | Deno et al. | .................... | 607/18 |
| 6,102,874 A | 8/2000 | Stone et al. | ................. | 600/595 |
| 6,275,727 B1 | 8/2001 | Hopper et al. | .............. | 600/513 |
| 6,280,409 B1 | 8/2001 | Stone et al. | ................... | 604/67 |
| 6,314,323 B1 | 11/2001 | Ekwall | ......................... | 607/23 |
| 6,490,472 B1 * | 12/2002 | Li et al. | ...................... | 600/410 |
| 6,572,557 B2 | 6/2003 | Tchou et al. | ................ | 600/483 |
| 2001/0037067 A1 | 11/2001 | Tchou et al. | ................ | 600/483 |
| 2002/0193839 A1 | 12/2002 | Cho et al. | ...................... | 607/17 |
| 2004/0059237 A1 * | 3/2004 | Narayan et al. | ............. | 600/509 |

(Continued)

FOREIGN PATENT DOCUMENTS

EP 1 070 516 A2 1/2001

(Continued)

OTHER PUBLICATIONS

Takeshi Tomita, M.D., et al., "*Role of Autonomic Tone in the Initiation and Termination of Paroxysmal Atrial Fibrillation in Patients Without Structural Heart Disease*," *J Cardiovasc Electrophysiol*; vol. 14, No. 6 (2003), pp. 559-564.

(Continued)

*Primary Examiner*—Carl H Layno
*Assistant Examiner*—Deborah Malamud

(57) ABSTRACT

An exemplary method includes selecting a cross-correlation frequency having an associated cross-correlation period, detecting and binning a heart rate in a heart rate bin, detecting and binning an activity state in an activity state bin, repeating the detecting and binning a heart rate and the detecting and binning an activity state during a cross-correlation period, and summing the products a bin count of the heart rate bins and a bin count of the activity state bins to provide a cross-correlation index for the cross-correlation period. Other exemplary algorithms, methods, devices, systems, etc., are also disclosed.

8 Claims, 10 Drawing Sheets

U.S. PATENT DOCUMENTS

2004/0186527 A1* 9/2004 Rouw et al. .................. 607/17

FOREIGN PATENT DOCUMENTS

EP 1 070 516 A3 4/2004

OTHER PUBLICATIONS

M. Facchini, et al., "*Changes of Autonomic Cardiac Profile After a 3-Week Integrated Body Weight Reduction Program in Severely Obese Patients,*" J. Endocrinol. Invest., 2003; vol. 26 (2), pp. 138-142.

M. Matveev, et al., "*Time-Related Heart Autonomic Balance Characteristics in Healthy Subjects,*" Physiol. Meas.., 2003; vol. 24 (3), pp. 727-743.

* cited by examiner

EXEMPLARY SCENARIO 300

EXEMPLARY SCENARIO 500

NON-PACED RATE

EXEMPLARY SCENARIO 600

NON-PACED RATE

EXEMPLARY SCENARIO 800

DAY 1 - ACTIVITY 810

DAY 1 - RATE 812

DAY 1 - ANALYSIS 814

$F_1$ = 15 MINUTES
$F_2$ = 1 DAY $F_2/F_1$ = 96 COUNTS/DAY $\sum_{I=1-25}$ ACT(I) * RATE(I)

= INDEX DAY 1
= 492

DAY 5 - ACTIVITY 820

DAY 5 - RATE 822

DAY 5 - ANALYSIS 824

$F_1$ = 15 MINUTES
$F_2$ = 1 DAY $F_2/F_1$ = 96 COUNTS/DAY $\sum_{I=1-25}$ ACT(I) * RATE(I)

= INDEX DAY 5
= 447

EXEMPLARY PROGRAMMING SYSTEM
1000

COLLECTING AND ANALYZING SENSED INFORMATION AS A TREND OF HEART FAILURE PROGRESSION OR REGRESSION

TECHNICAL FIELD

Exemplary mechanisms presented herein generally relate to cardiac pacing and/or stimulation therapy. Various exemplary mechanisms concern binning and analyzing sensed information, which optionally reduces data storage requirements.

BACKGROUND

Conventional implantable stimulation devices for cardiac therapy often sense information associated with cardiac performance. A care provider may use such information to adjust cardiac stimulation therapy or to recommend other therapy while some implantable stimulation devices can use such information to automatically adjust therapy (e.g., according to an adjustment algorithm). In either instance, the amount of information available to the care provider or the adjustment algorithm may be limited by storage capabilities of the implantable stimulation device. For example, if a device measures and stores heart rate every minute, then after one week the device would have stored over 10,000 heart rate values. For a consultation schedule of once every three months, the device would have stored about 130,000 heart rate values. For heart rate values of 8 bits each (e.g., 1 byte), the storage requirements would be about 130,000 bytes. While some conventional implantable stimulation devices may have storage capabilities in excess of 100,000 bytes, choices still need to be made as to how to best use the limited storage capabilities. Thus, some devices rely on data reduction techniques to reduce storage needs.

Data reduction techniques include averaging, binning, modeling, etc. In the above example, a running average of 1 hour for heart rate values will reduce storage needs by a factor of 60. Binning, which is usually associated with histograms, can also reduce storage needs. For example, if a patient experiences a heart rate of 60 bpm one thousand times over a three month period, binning would store a representation of 1,000 in a 60 bpm bin as opposed to storing all 1,000 heart rate values. In this example, however, time may be lost in that the binning does not register a time for each bin count.

In general, choices need to be made that balance requirements for diagnostic information and storage capabilities. As described below, various exemplary data reduction algorithms aim to retain the diagnostic value of information while optionally reducing storage requirements.

SUMMARY

An exemplary method includes selecting a cross-correlation frequency having an associated cross-correlation period, detecting and binning a heart rate in a heart rate bin, detecting and binning an activity state in an activity state bin, repeating the detecting and binning during a cross-correlation period, and summing the products of a bin count of the heart rate bins and a bin count of the activity state bins to provide a cross-correlation index for the cross-correlation period. Other exemplary algorithms, methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Various exemplary algorithms, as implemented in methods, devices, systems, etc., aim to retain the diagnostic value of information while optionally reducing storage requirements. An exemplary method includes binning of measured values for two variables and calculating a cross-correlation value based on the bin counts for the two variables. The binning and calculating may be performed according to any selected frequencies wherein the binning frequency is greater than the calculating frequency. In general, a measuring or sensing frequency is greater than the binning frequency.

In a specific example, a relationship is noted between heart rate and activity wherein heart rate increases with respect to an increase in activity. In this example, a histogram for heart rate and a histogram for activity will have certain shapes for a normal patient and certain other shapes for a patient experiencing increased sympathetic activity and/or decreased parasympathetic activity. In particular, a cross-correlation value for the normal patient case will be greater than a cross-correlation value for the patient experiencing a change in autonomic activity. Thus, a record of the cross-correlation value over time can indicate whether a patient is experiencing a change in autonomic activity. Further, an exemplary algorithm may choose to store cross-correlation values and overwrite or delete bin counts. Such an exemplary algorithm aims to retain diagnostic information while reducing associated storage needs.

An exemplary implantable stimulation device, suitable for implementation of various exemplary algorithms, is described followed by examples wherein binning and calculating occur. An exemplary programmer may download calculated values and analyze and/or present the values to a care provider.

Exemplary Stimulation Device

The techniques described below are intended to be implemented in connection with any stimulation device that is configured or configurable to stimulate nerves and/or stimulate and/or shock a patient's heart.

Figure 1:
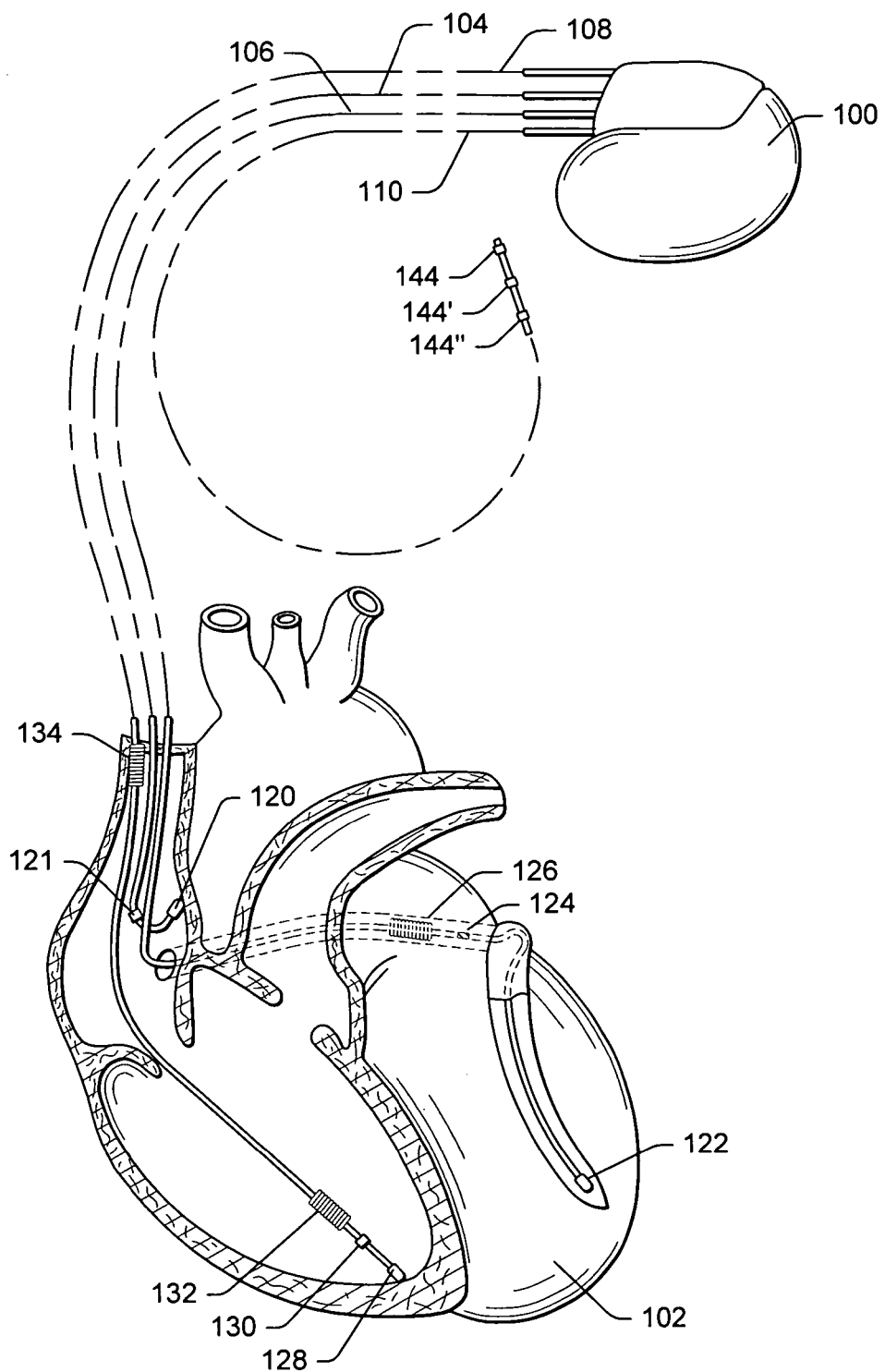
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
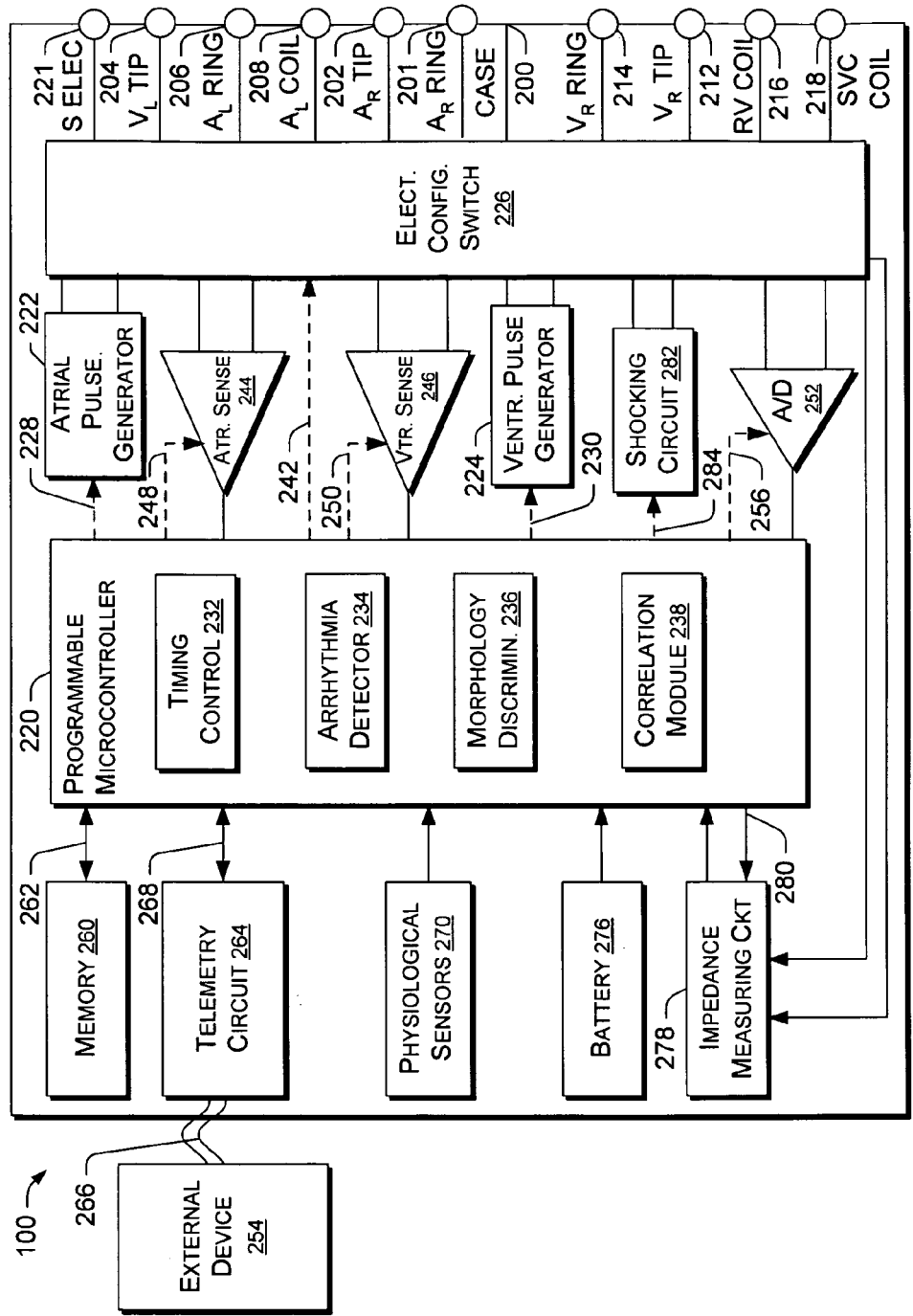
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depictirig various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a correlation module 238 that may perform a variety of tasks related to binning, histograms, analyzing, correlations, etc. This component can be utilized by the stimulation device 100 for determining desirable therapies. The correlation module 238 may be implemented in hardware as part of the microcontroller 220, or as software/firmware instructions programmed into the device and executed on the microcontroller 220 during certain modes of operation. Such a module may include other capabilities related to other functions that may be germane to analyzing binned information.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, W delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrio-ventricular nodal conduction, and ventricular contractile force, also known as contractility or inotropy. Sympathetic efferent postganglionic neurons, when stimulated, generally increase heart rate and increase contractility. Note that contractility may be associated with the term "inotropy", heart rate with the term "chronotropy" and conduction velocity with the term "dromotropy".

Regarding parasympathetic pathways, vagi nerves distributed to regions of the SA node and the AV node provide for at least some parasympathetic effects on the heart. Parasympathetic nerves can release acetylcholine to these regions which typically results in both a decrease in the rate of rhythm of the SA node, as well as a decrease in the cardiac impulse transmission into the ventricles. In general, the right vagus innervates the SA nodal region, the atrial muscle and, to a much lesser degree, the AV nodal region; whereas, the left vagus nerve innervates the SA nodal region and atrial muscle to a lesser degree than it innervates the AV nodal region. Stimulation of the right vagus nerve can slow the SA node rate and thereby reduce heart rate; whereas, stimulation of the left vagus nerve can produce some slowing of the SA node, prolongation of AV conduction and partial or total AV block.

Regarding sympathetic stimulation, norepinephrine is released by sympathetic nerves. After its release, norepinephrine acts on the sino-atrial node (SA node) to increase the rate of diastolic depolarization, and thereby increase heart rate, and acts on the atrio-ventricular node (AV node) to increase the velocity of conduction and diminish the refractory period during which the AV node is unresponsive to stimuli coming from the atrium.

Cardiac output (CO) depends on heart rate (HR) and stroke volume (SV) (e.g., CO equals HR times SV). Changes in ventricular contractility alter the rate of force and pressure development by the ventricle(s) and therefore change the rate of ejection (i.e., ejection velocity). Another term used to describe cardiac operation is "cardiac workload", which is sometimes defined as the product of systolic blood pressure and heart rate. In general, an increase in inotropy, chronotropy and/or dromotropy result in an increase in cardiac workload. Further, sympathetic activity is likely to increase cardiac workload whereas parasympathetic activity is likely to decrease cardiac workload.

Figure 3:
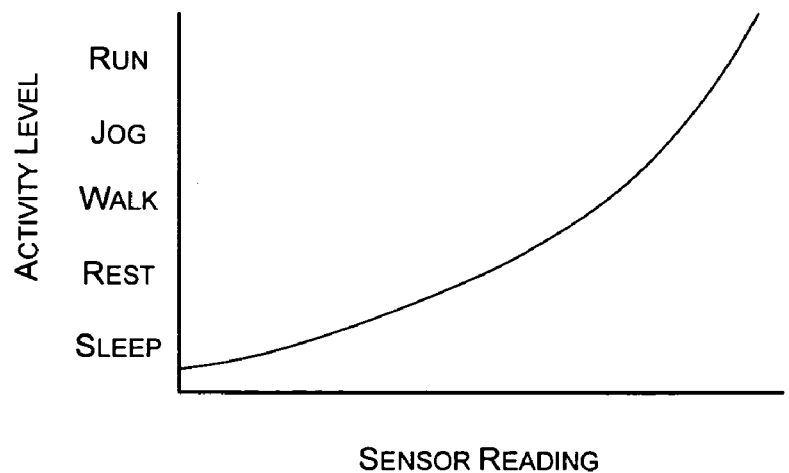
FIG. 3 is an exemplary scenario that includes a plot of activity level or state as a function of sensor reading and a histogram of counts versus activity level or state.
Figure 3:
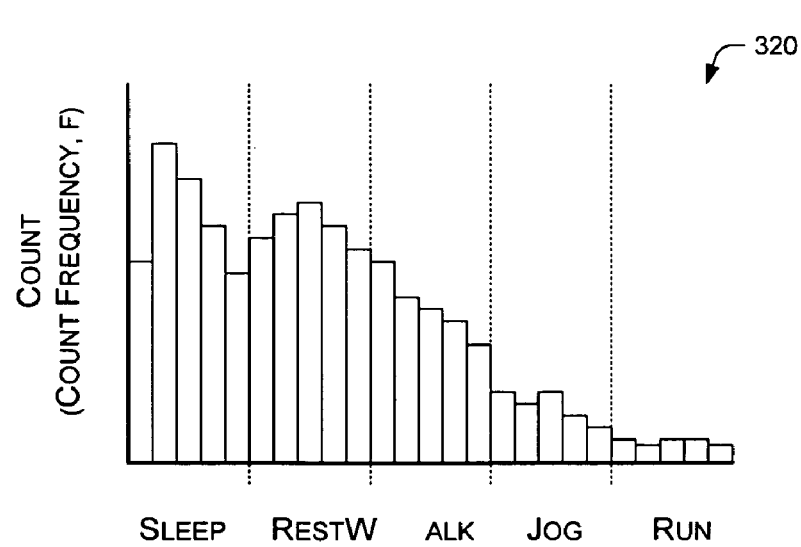

FIG. 3 shows an exemplary scenario 300 for sensing and binning activity. A plot 310 of activity level versus sensor reading indicates that some known relationship or calibration curve exists between sensor reading and activity level. Such a relationship and/or calibration curve may depend on more than one sensor reading. For purposes of explaining various algorithms, the activity level has been defined as including sleep, rest, walk, jog and run states. Such states correspond generally to increasing levels of activity. Of course, any of a variety of states may be selected or, alternatively, sensor readings indicative of activity may be stored wherein some known relationship exists between heart rate sensor readings and the activity sensor readings. Such a known relationship allows for analysis of cross-correlation values. For example, for a normal patient, an increase in a sensor reading for activity will usually correspond to an increase in a sensor reading for heart rate. Of course, other known relationships may exist.

The exemplary scenario 300 includes a histogram 320 of count versus activity state for a count frequency f. The histogram 320 is representative of a normal patient wherein the count frequency is about 24 hours. According to the histogram 320, each activity state includes five sub-states for a total of 25 bins. Of course, other number of states and/or sub-states may exist to provide a same or different number of bins.

In general, the histogram 320 includes historical information. Such information is optionally filtered or otherwise conditioned. For example, a forgetting factor may be used to weight information based on age of the information. Thus, the relevance of certain information may diminish over time. A variety of techniques exist by which to change weight or relevance of information over time, in response to one or more events, etc.

Distributions such as the histogram distribution 320 may be analyzed to obtain mean, mode, median, skew, and other values. Such values may be used in conjunction with other techniques presented herein. For example, with reference to the plot 900 of FIG. 9, mean, mode, median, skew and/or other values may be plotted to assist in analysis of any particular comparison and/or in analyzing trends.

Figure 4:
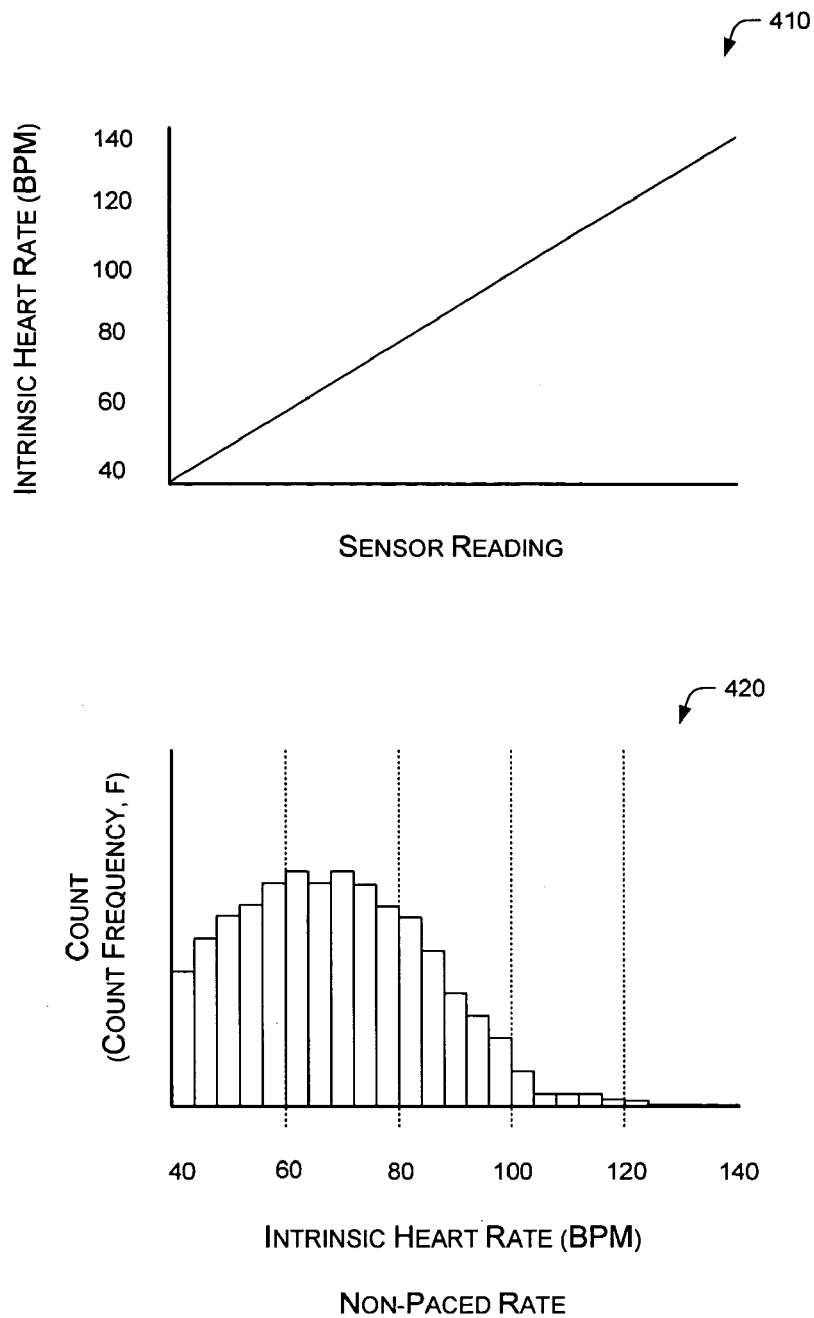
FIG. 4 is an exemplary scenario that includes a plot of intrinsic heart rate as a function of sensor reading and a histogram of counts versus intrinsic heart rate.

FIG. 4 shows an exemplary scenario 400 for sensing and binning heart rate. A plot 410 of heart rate versus sensor reading indicates that some known relationship or calibration curve exists between sensor reading and heart rate. Such a relationship and/or calibration curve may depend on more than one sensor reading. For purposes of explaining various algorithms, heart rate has been defined in terms of beats per minute (bpm). Of course, any of a variety of rates or intervals may be selected or, alternatively, sensor readings indicative of heart rate may be stored wherein some known relationship exists between heart rate sensor readings and the activity sensor readings. Such a known relationship allows for analysis of cross-correlation values. For example, for a normal patient, an increase in a sensor reading for activity will usually correspond to an increase in a sensor reading for heart rate. Of course, other known relationships may exist.

The exemplary scenario 400 includes a histogram 420 of count versus heart rate for a count frequency f. The histogram 420 is representative of a normal patient wherein the count frequency is about 24 hours. According to the histogram 420, a total of 25 heart rate bins exist. Of course, another number of bins may be selected.

In general, the histogram 420 includes historical information. Such information is optionally filtered or otherwise conditioned. For example, a forgetting factor may be used to weight information based on age of the information. Thus, the relevance of certain information may diminish over time. A variety of techniques exist by which to change weight or relevance of information over time, in response to one or more events, etc.

Distributions such as the histogram distribution 420 may be analyzed to obtain mean, mode, median, skew, and other values. Such values may be used in conjunction with other techniques presented herein. For example, with reference to the plot 900 of FIG. 9, mean, mode, median, skew and/or other values may be plotted to assist in analysis of any particular comparison and/or in analyzing trends.

Figure 5:
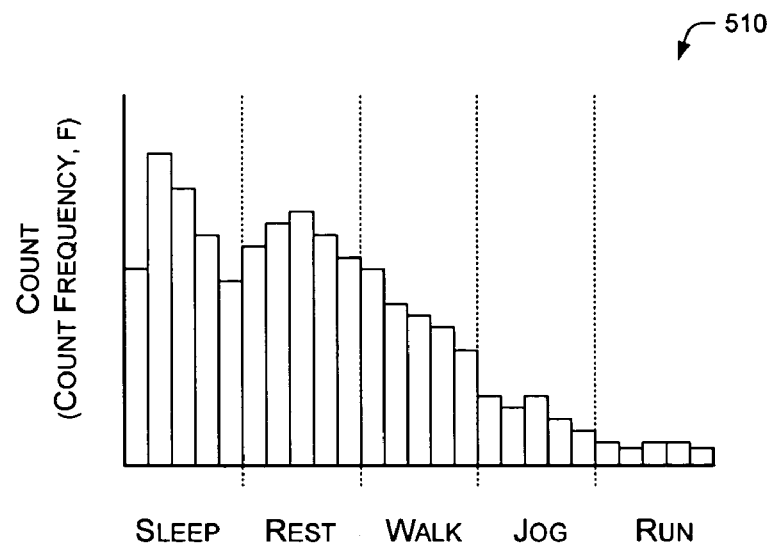
FIG. 5 is an exemplary normal scenario that includes two related histograms, one for counts versus activity bin and the other for counts versus intrinsic heart rate bins.
Figure 5:
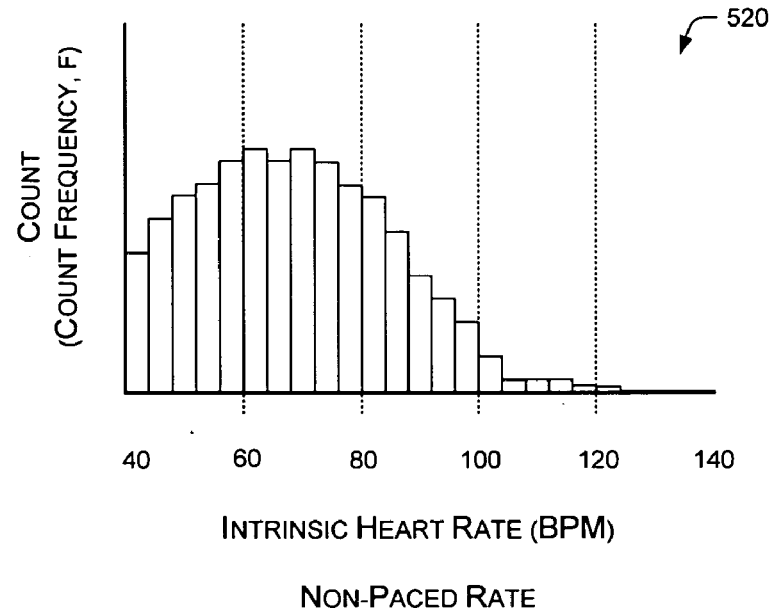

FIG. 5 shows an exemplary scenario 500 that includes an activity histogram 510 and a heart rate histogram 520. This pair of historical information may be compared to another pair of historical information for a variety of purposes including diagnostics, cardiac therapy, etc. For example, an exemplary method includes providing two pairs of historical information, comparing the two pairs and then optionally adjusting therapy delivered by an implantable device in response to the comparing. In this example, the providing may be achieved via sensing using an implantable device. Information obtained via a comparison of two pairs of historical information is optionally communicated from an implantable device to another device, for example, telemetrically or by other means.

The activity histogram 510 and the heart rate histogram 520 have a count frequency, f. The heart rate histogram 520 corresponds to intrinsic heart rate while in other scenarios paced and/or intrinsic heart rate may be considered. While, in general, intrinsic heart rate provides more beneficial diagnostic information as it represents a physiological response to activity level (e.g., autonomic activity response, etc.), an adjustable pacing rate may also provide beneficial information as it may vary in response to a change in physiology.

Figure 6:
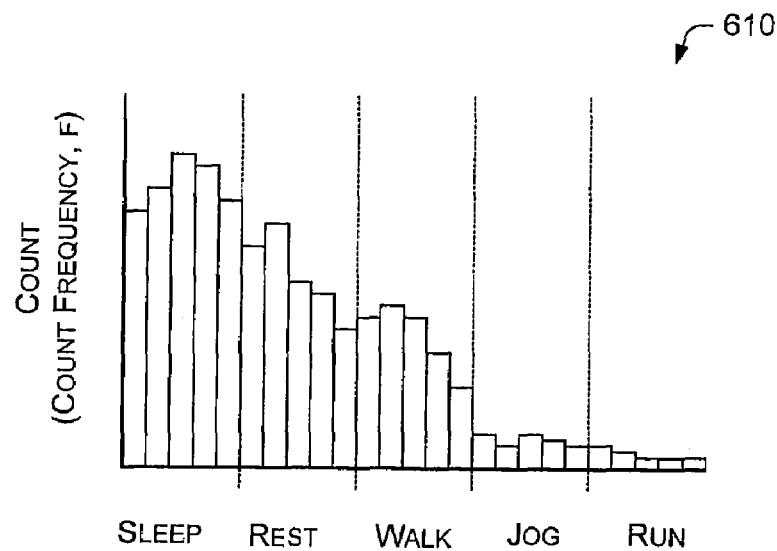
FIG. 6 is an exemplary abnormal scenario (e.g., increased sympathetic activity and/or decreased parasympathetic activity) that includes two related histograms, one for counts versus activity bin and the other for counts versus intrinsic heart rate bins.
Figure 6:
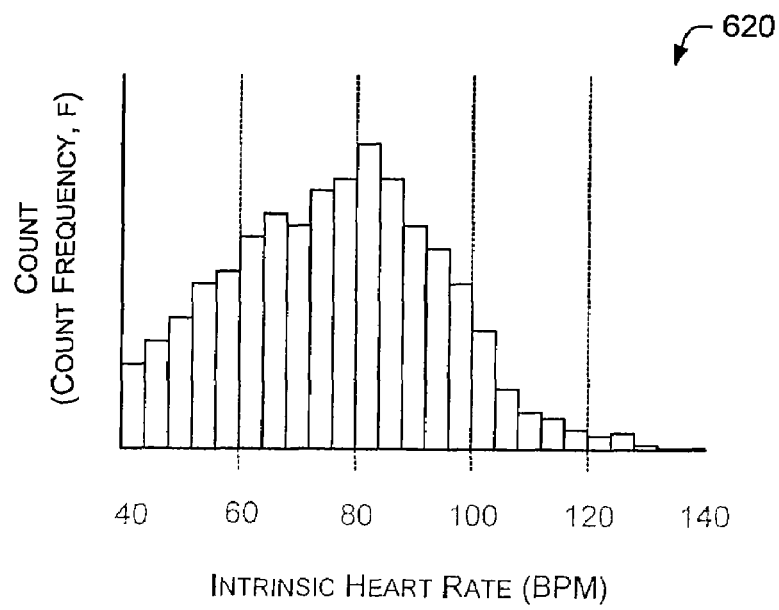

FIG. 6 shows an exemplary scenario 600 that includes an activity histogram 610 and a heart rate histogram 620. The two histograms 610, 620 may be considered a pair of historical information corresponding to two different physiological and/or therapeutic parameters. The activity histogram 610 and the heart rate histogram 620 have a count frequency, f. The heart rate histogram 620 corresponds to intrinsic heart rate while in other scenarios paced and/or intrinsic heart rate may be considered.

A comparison of the information of scenario 500 to the information of scenario 600 indicates that the scenario 600 corresponds to a greater sympathetic tone or a lesser parasympathetic tone. In particular, the histograms of scenario 600 include more low activity bin counts and more high heart rate bin counts than the histograms of scenario 500. Such a comparison indicates that the heart is working harder in the scenario 600 than in the scenario 500. In addition, a patient's activity level may decrease in response to symptoms associated with heart failure. If the heart is working harder, the increase in work may speed the progression of congestive heart failure and hence may be important to address.

Figure 7:
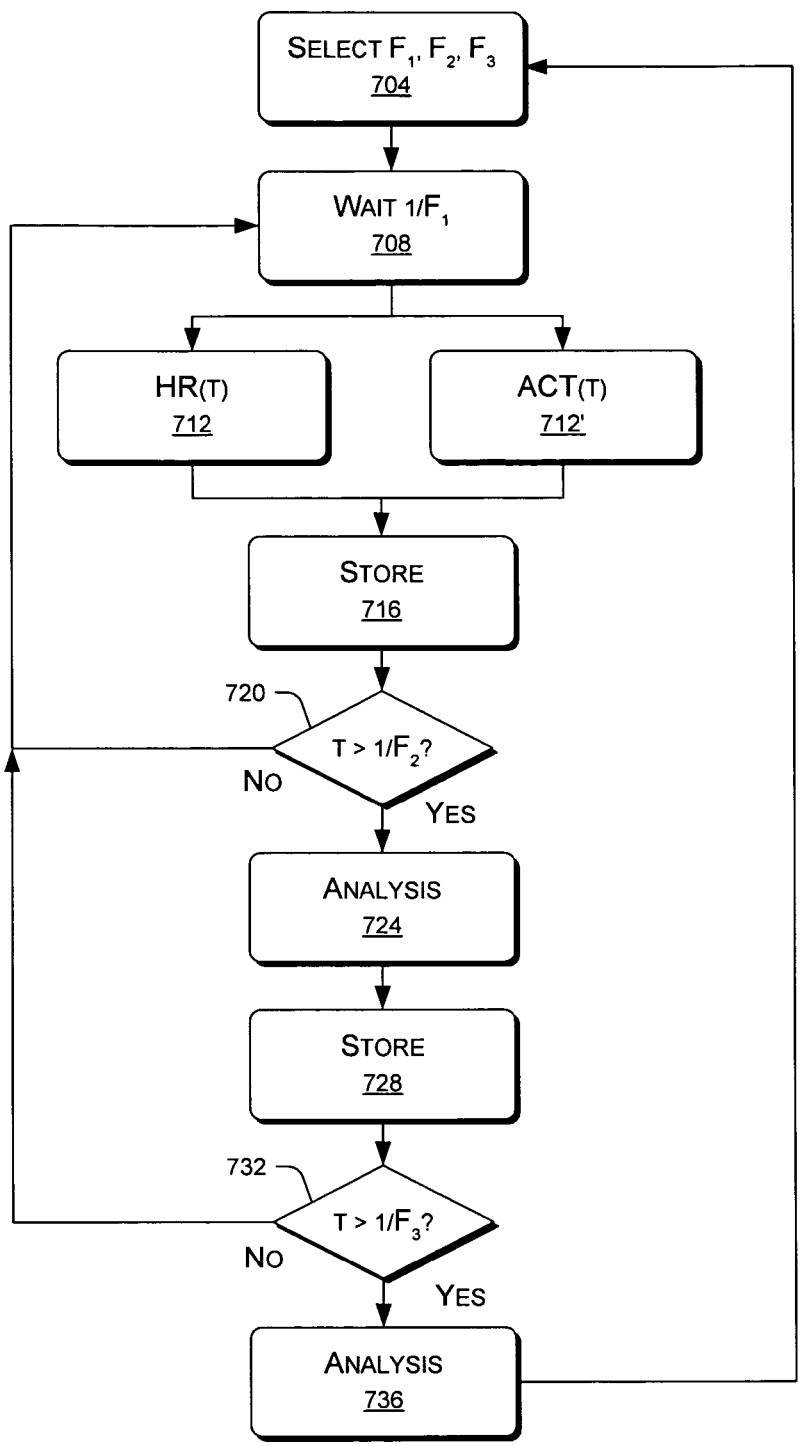
FIG. 7 is an exemplary method for selecting frequencies, sensing information, binning the sensed information and analyzing the binned information.

FIG. 7 shows an exemplary method 700 for analysis of binned information such as that presented in the histograms of the exemplary scenarios 500 and 600. In a selection block 704, various frequencies are selected. For example, frequency f1 corresponds to a measurement or sensing frequency, frequency f2 corresponds to a calculation frequency (e.g., a cross-correlation frequency), and frequency f3 corresponds to a consultation frequency (e.g., office consultation, telephonic consultation, information download frequency, etc.).

A wait block 708 implements a wait period of 1/f1. After the wait period two measurement blocks 712, 712' act to measure heart rate, HR(t), and activity level, ACT(t), respectively. Of course, measurement may occur on a more frequent basis together with some averaging, etc., however, according to the exemplary method 700, the measurements of the block 712, 712' also correspond to a storage frequency, per the storage block 716. Thus, the storage block 716 stores a heart rate value and an activity level value at a frequency f1. In this example, the storage block 716 includes binning. Thus, at block 716, the exemplary method 700 bins the heart rate value and the activity value. The binning results in bin counts for a heart rate histogram and bin counts for an activity level histogram.

A decision block 720 follows the storage block 716 which decides if a time period corresponding to the frequency f2 has expired. If the decision block 720 decides that the period has not expired, then the method 700 continues in the wait block 708. However, if the period has expired, then the method 700 continues in an analysis block 724. The analysis block 724 may calculate a cross-correlation value based on the bin counts for heart rate and the bin counts for activity level. The cross-correlation value may be calculated by multiplying a bin count for each heart rate bin by a bin count of a corresponding activity level bin and then summing the products to result in a single value. In general, a one-to-one correspondence exists between heart rate bins and activity level bins (see, e.g., the scenarios 500, 600). Of course, in situations where the number of heart rate bins and activity level bins differ, an analysis block may account for such differences as appropriate. A storage block 728 acts to store the single value from the analysis. In general, the value is stored in a manner wherein time may be inferred and/or wherein a time stamp or other time information is included.

A decision block 732 follows the storage block 728 wherein a decision is made as to whether a period of 1/f3 has expired. If the period has not expired, then the method 700 continues in the wait block 708. However, if the period has expired, then the method 700 continues in an analysis block 736. The analysis block 736 typically involves downloading of the values stored in the storage block 728. Of course, where sufficient memory exists, in an alternative exemplary method, the analysis block 724 and the storage block 728 may occur according to the frequency f3. The analysis block 736 may include analysis using a programmer or other external computing device.

Figure 8:
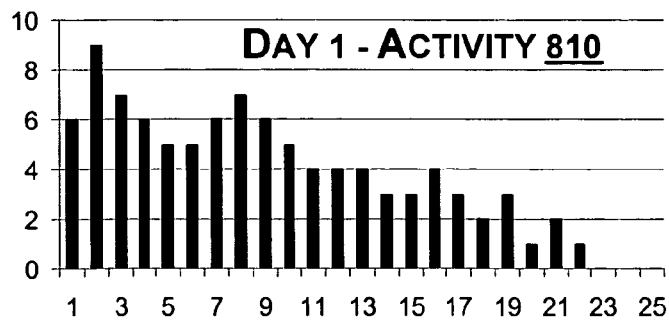
FIG. 8 is an exemplary scenario for two days that includes analyses of binned information resulting in a daily index.
Figure 8:
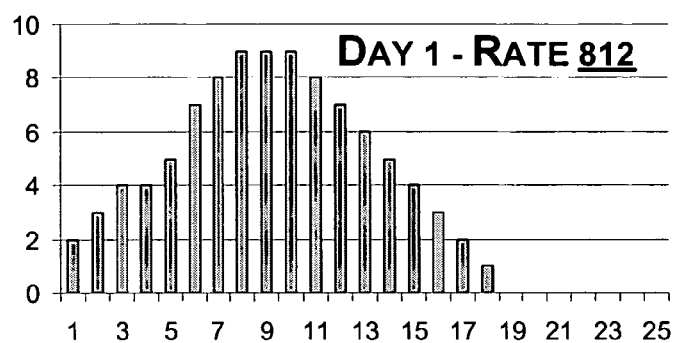
Figure 8:
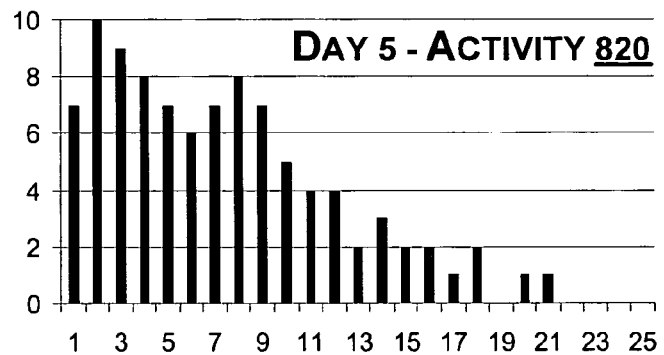
Figure 8:
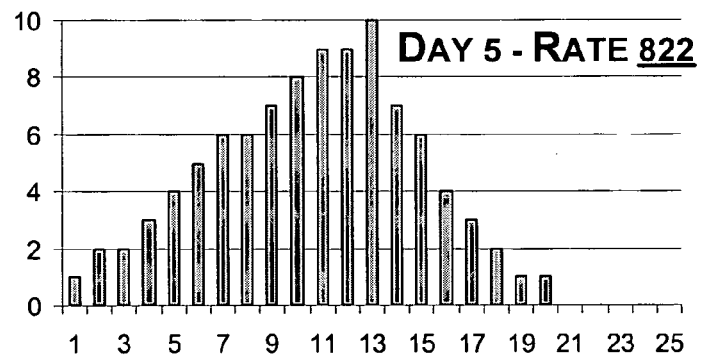

FIG. 8 shows an exemplary scenario 800 that compares two days of information. Day 1 information includes an activity level histogram 810 and a heart rate histogram 812. An analysis 814 of the information indicates that f1 is 15 minutes, f2 one day to thereby generate 96 counts per day. Given 25 bins for each of the histograms 810, 812, an index for Day 1 is 492. Day 5 information includes an activity level histogram 820 and a heart rate histogram 822. An analysis 824 of the information indicates that f1 is 15 minutes, f2 one day to thereby generate 96 counts per day. Given 25 bins for each of the histograms 810, 812, an index for Day 5 is 447. Thus, as explained above, a comparison of the Day 1 index and the Day 5 index indicates that sympathetic activity has increased and/or parasympathetic activity has decreased.

Figure 9:
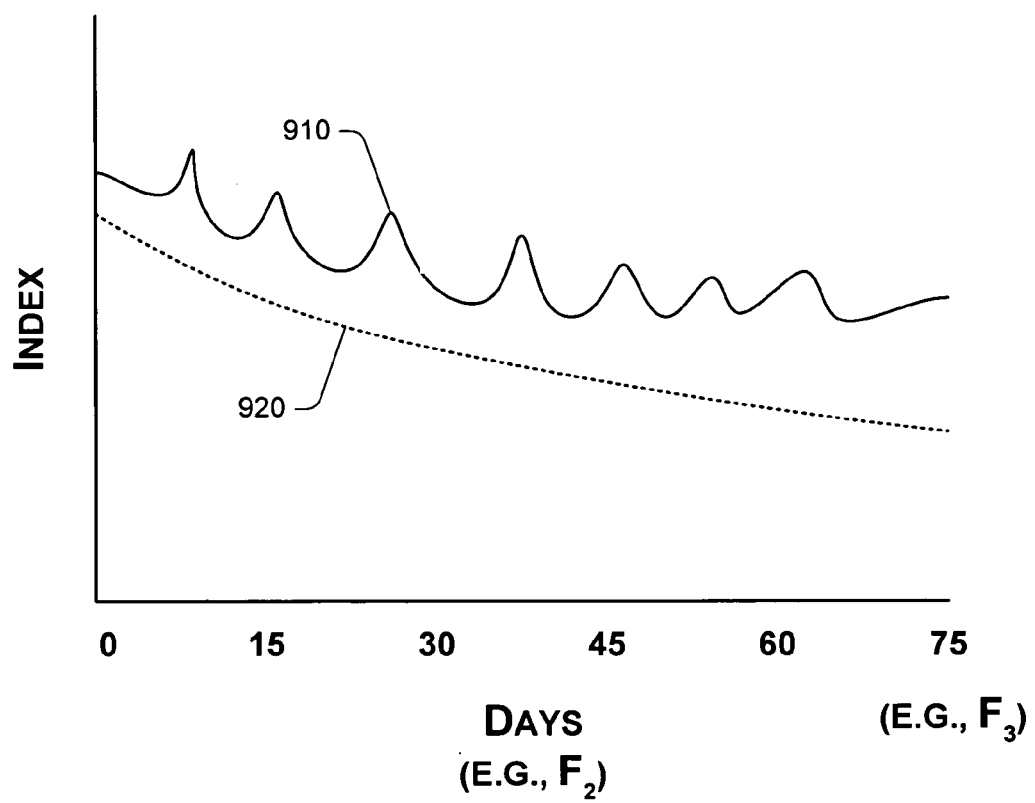
FIG. 9 is an exemplary plot of daily index versus days for two different scenarios.

FIG. 9 shows an exemplary plot 900 of index value versus days (e.g., f2) for a period of about 1/F3 (e.g., 75 days). A first set of values 910 shows peaks which may correspond to exercise, medication and/or relaxation days. In general, such activities or medication may be exhibited in the index values and hence enhance diagnosis of cardiac and/or lifestyle issues. A second set of values 920 shows a steady decline in the index over the 75 day period.

While various examples include a daily frequency for histograms (e.g., a typical behavioral human cycle length) other examples may have a frequency or time divisions or time periods less than a day. For example, a day may be broken into a sleep period, a morning period, an afternoon period and an evening period. Further, bin counts or histograms may be stored for such subdivisions of a day. In this example, an index may be calculated for a sleep period, a morning period, an afternoon period and an evening period. Such information may be analyzed over a period of days. For example, a plot of sleep period index over three months may indicate a certain increase in sympathetic activity during sleep while a plot of afternoon index may indicate a certain decrease in sympathetic activity during the afternoon. A comparison between these two sets of information may aid in diagnosing issues and/or selecting therapy. Various studies indicate that autonomic tone varies throughout a day hence such information may help diagnose deviations from a "normal" daily variation.

While use of daily subdivisions may in some implementations require more storage, the use of such will typically result in less storage requirements when compared to conventional techniques. Further, the subdivision information may be combined to produce a daily result, either by an exemplary implantable device or an external device, without encountering significant computational overhead.

With respect to the various studies regarding daily variation in autonomic tone, a study by Matveev et al., "Time-related heart autonomic balance characteristics in healthy subjects", *Physiol Meas.*, August;24(3):727-43 (2003), examined changes of the heart autonomic balance between morning (8-9 h) and afternoon (14-15 h) in 22 healthy subjects wherein the selection of these two daytime periods was substantiated by the established higher risk of cardiovascular incidents in the morning and the relative balance of the vegetative nervous system in the afternoon hours. Result of this study indicated that "in spite of the relative stability of the vegetative nervous system in healthy subjects, hypersympatheticotonia and relatively lower parasympathetic tone were present in the risky morning hours". Hence, the daily subdivisions approach may help to track changes in autonomic tone during various daytime periods.

Another study by Facchini et al., "Changes of autonomic cardiac profile after a 3-week integrated body weight reduction program in severely obese patients", *J Endocrinol Invest.* Feburary;26(2):138-42 (2003), noted that autonomic control of the heart is abnormal in obese subjects due to a prevalence of sympathetic over parasympathetic limb of the autonomic balance. The study by Facchini et al. concluded using Holter recording data that "a short-term, integrated body weight reduction program is able to favorably modify the autonomic profile in a population of normotensive, severely obese subjects". They also noted that "the reduction of heart rate and the increase in parasympathetic activity may consistently contribute to a reduction of the risk of cardiovascular morbidity and of sudden cardiac death, still high in this patients' group".

Yet another study by Tomita et al., "Role of autonomic tone in the initiation and termination of paroxysmal atrial fibrillation in patients without structural heart disease", *J Cardiovasc Electrophysiol.*, June;14(6):559-64 (2003), noted that "previous studies have suggested that paroxysmal atrial fibrillation (PAF) of vagal origin often occurs at night and PAF of sympathetic origin occurs during the daytime; however, autonomic tone after spontaneous termination of PAF has not been determined". Tomita et al. aimed to evaluate by heart rate variability (HRV) analysis the relationship between the time of PAF onset and autonomic tone before and after PAF and concluded that "the autonomic nervous system plays an important role in both the initiation and termination of PAF" and that "the time of PAF onset influences the autonomic tone at the initiation and termination of PAF". Again, information provided by various exemplary methods, devices and/or systems presented herein can help diagnose issues and/or improve therapy.

Various exemplary methods optionally include multiplying values selected from two sets of binned data and then analyzing the result(s) for changes over time. For example, an analysis may rely on skewedness, mean shifting, heteroskedacity or other techniques to determine whether a change in cardiac condition has occurred.

Various exemplary methods optionally analyze a mean, mode, median, etc., of heart rate in relation to a mean, mode, median, etc., of activity as a sanity check or to otherwise help determine cardiac condition. Weighting of bins, optionally a time varying weight, may be used prior to or during an analysis to determine cardiac condition or a change thereto. Pairing of different data (e.g., heart rate and activity, etc.) may occur wherein for example a first pair and a second pair are compared to help determine cardiac condition. Various exemplary methods optionally include adjusting therapy delivered by an implantable device in response to an analysis.

Figure 10:
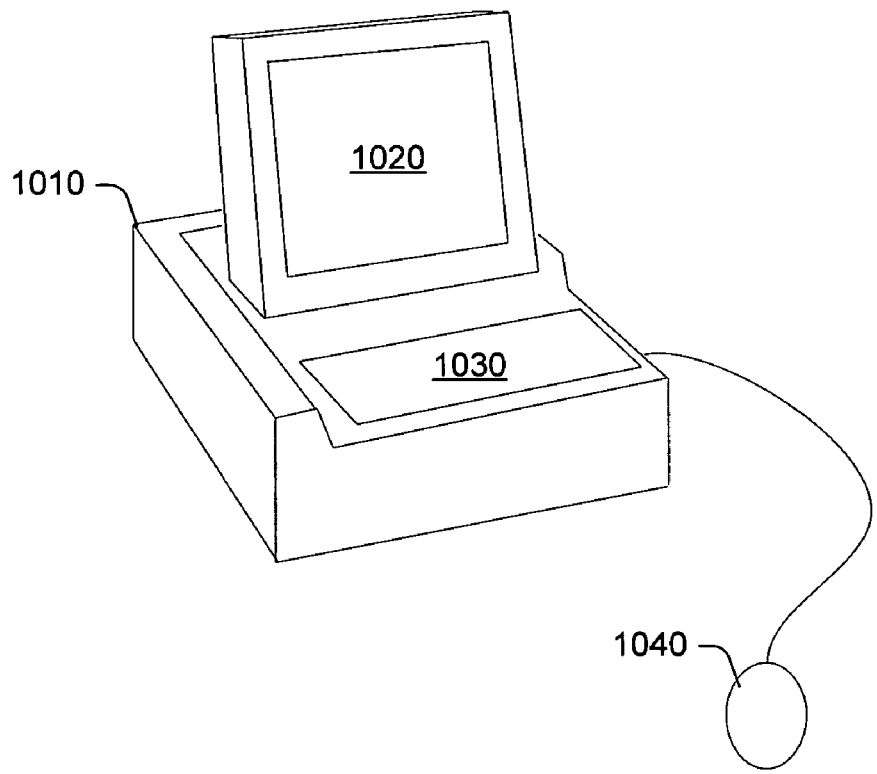
FIG. 10 is a diagram of an exemplary programming system capable of use with various exemplary methods, devices and/or systems.

FIG. 10 shows an exemplary programming system 1000 for communicating with an implanted device. The exemplary programming system 1000 includes a computer 1010, a display 1020, a keyboard 1030 and a telemetry probe 1040. The telemetry probe 1040 allows for communication with an implanted device. In general, such a probe is placed in proximity to an implanted device and communication is established via radio frequency transmission.

The term "programmer" or "programming system" is commonly used in the implanted device industry to describe a computing system that includes hardware and software that can operate to communicate with an implanted device. For example, St. Jude Medical, Inc. (St. Paul, Minn.) markets the Model 3510 programming system that includes a computer system-based programmer. Thus, in one example, the exemplary programming system 1100 includes various features of the Model 3510 programming system. The Model 3510 programming system includes a custom, portable computer system that features a large, color display on a touch-sensitive, active matrix LCD screen. The Model 3510 programmer can provide continuous, simultaneous display of surface ECGs, intracardiac electrograms, annotated event markers, and Electronic Calipers™, where an A paced and V sensed interval (e.g., AR interval) is automatically measured and reported, for example, on the programmer screen. The Model 3510 includes a full-size keyboard that allows for easy input of patient and other information. An automated follow-up feature guides this process and generates custom reports quickly and easily. The programmer then prints reports on a full-size sheet of paper for easy insertion into patient charts. The Model 3510 programming system is lightweight for easy portability. In addition, it can interface with various commercially available data management systems.

More specific features of the Model 3510 programming system include customizable automatic follow-up protocols; archive data storage that offers the ability to view and print information acquired during previous follow-up sessions; detection, therapy, and episode summaries; and lifetime diagnostics, including pacing and charging history and event, heart rate, and sensor information histograms.

As described herein, the exemplary programming system 1000 includes an ability to download binned and/or calculated information and/or other information from an implantable or implanted device. For example, such an exemplary programming system optionally includes hardware and/or software capable of downloading, analyzing and/or displaying the exemplary information of FIGS. 8 and 9.

While various exemplary algorithms, methods, devices, systems, etc., refer to heart rate and activity, other examples may rely on different physiological measures. For example, an exemplary method may include selecting a cross-correlation period, detecting and binning a first physiological measure in a first physiological measure bin, detecting and binning a second physiological measure in a second physiological measure bin, repeating the detecting and binning a first physiological measure and the detecting and binning a second physiological measure during the cross-correlation period, and summing the products of a bin count of the first physiological measure bins and a bin count of the second physiological measure bins to provide a cross-correlation index for the cross-correlation period. In general, some relationship exists between the first physiological measure and the second physiological measure. For example, if a change in the cross-correlation index indicates a change in autonomic activity, then a relationship may exist between the two physiological measures.

CONCLUSION

Although exemplary methods, devices and/or systems have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices and/or systems.

What is claimed is:

1. A method comprising:
   detecting and binning a value of a first physiological measure;
   detecting and binning a value of a second physiological measure the second physiological measure being different from the first physiological measure;
   repeating the detecting and binning one or more times;
   multiplying a bin count for the first physiological measure bins with a corresponding bin count of the second physiological measure bins to form a product of each of the bin count of the first physiological measure bins and the corresponding bin count of the second physiological measure bins;
   summing the products of the bin counts of the first physiological measure bins and the bin counts of the second physiological measure bins to provide a cross-correlation index; and
   adjusting a cardiac stimulation therapy delivered by an implantable medical device based at least in part on the cross-correlation index.

2. The method of claim 1 wherein a change in the cross-correlation index indicates a change in autonomic activity.

3. The method of claim 1 further comprising storing the cross-correlation index and subsequently downloading the stored cross-correlation index to another device.

4. The method of claim 1 further comprising plotting the cross-correlation index with one or more other cross-correlation indexes versus time.

5. The method of claim 1 wherein one of the physiological measures comprises heart rate.

6. The method of claim 1 wherein one of the physiological measures comprises activity.

7. An implantable stimulation device comprising
   one or more sensors configured to detect values of first and second physiological measures wherein the second physiologic measure is different from the first physiologic measure;
   memory configured to bin the value of the first physiologic measures in first physiologic bins and the second physiologic measures in second physiologic measures bins;
   pulse generator capable of delivering a cardiac stimulation pulse; and
   control logic configured to multiply a bin count of the first physiological measure bins with a bin count of the corresponding second physiological measure bins to form a product of each of the bin count of the first physiological measure bins and the bin count of the corresponding second physiological measure bins and to sum the products of the bin count of the first physiological measure bins and the bin count of the second physiological measure bins to provide a cross-correlation, wherein the control logic is further configured to adjust a cardiac stimulation therapy based at least in part on the cross-correlation index.

8. The implantable stimulation device of claim 7 further comprising a telemetry circuit capable of communicating the cross-correlation index to another device.

* * * * *